US011529225B2

(12) United States Patent
Hartley (10) Patent No.: US 11,529,225 B2
(45) Date of Patent: Dec. 20, 2022

(54) THORACIC AORTA STENT GRAFT

(71) Applicant: Cook Medical Technologies LLC, Bloomington, IN (US)

(72) Inventor: David Ernest Hartley, Wannanup (AU)

(73) Assignee: Cook Medical Technologies LLC, Bloomington, IN (US)

( * ) Notice: Subject to any disclaimer, the term of this patent is extended or adjusted under 35 U.S.C. 154(b) by 186 days.

(21) Appl. No.: 16/900,014

(22) Filed: Jun. 12, 2020

(65) Prior Publication Data

US 2020/0306028 A1    Oct. 1, 2020

Related U.S. Application Data

(63) Continuation of application No. 16/511,516, filed on Jul. 15, 2019, now Pat. No. 10,779,931, which is a
(Continued)

(51) Int. Cl.
*A61F 2/07* (2013.01)
*A61F 2/856* (2013.01)
(Continued)

(52) U.S. Cl.
CPC ............... *A61F 2/07* (2013.01); *A61F 2/856* (2013.01); *A61F 2/89* (2013.01); *A61F 2/915* (2013.01);
(Continued)

(58) Field of Classification Search
CPC ............... A61F 2/07–2002/077; A61F 2/856
See application file for complete search history.

(56) References Cited

U.S. PATENT DOCUMENTS 6,187,033 B1    2/2001   Schmitt et al.
6,645,242 B1   11/2003   Quinn
(Continued)

FOREIGN PATENT DOCUMENTS

AU    2010202544 B1    8/2010
EP         1245202     10/2002
(Continued)

OTHER PUBLICATIONS

Examination report for corresponding EP Application No. 11703804.2-1651, dated Apr. 2, 2015, 6 pgs.
(Continued)

*Primary Examiner* — Rebecca S Preston
(74) *Attorney, Agent, or Firm* — Crowell & Moring LLP (57) ABSTRACT

A stent graft for placement in a vessel of a patient, the stent graft that has a tubular body of graft material, the tubular body having a proximal inflow end, a distal outflow end, a main lumen therethrough, a longitudinal access, and a sidewall from the first end to the second end. At least one stent is along the length of the tubular body. One or more shaped recesses are formed of a concave or recessed portion of graft material that extends into the lumen of the stent graft. A fenestration is in the recessed portion with a fenestration and an internal branch extends from the or each fenestration toward the proximal end of the tubular body of graft material. The internal branch may have a tubular portion and a funnel portion, wherein the tubular portion extends into the main lumen and the enlarged funnel portion is attached to sidewall and forms the at least one shaped recess.

21 Claims, 5 Drawing Sheets

Related U.S. Application Data continuation of application No. 16/287,239, filed on Feb. 27, 2019, now Pat. No. 10,485,651, which is a continuation of application No. 15/593,715, filed on May 12, 2017, now Pat. No. 10,231,822, which is a continuation of application No. 13/576,348, filed as application No. PCT/US2011/024148 on Feb. 9, 2011, now Pat. No. 9,649,188.

(60) Provisional application No. 61/302,586.

(51) Int. Cl.
  *A61F 2/954* (2013.01)
  *A61F 2/82* (2013.01)
  *A61F 2/06* (2013.01)
  *A61F 2/89* (2013.01)
  *A61F 2/915* (2013.01)

(52) U.S. Cl.
  CPC ......... *A61F 2/954* (2013.01); *A61F 2002/061* (2013.01); *A61F 2002/075* (2013.01); *A61F 2002/826* (2013.01); *A61F 2210/0014* (2013.01); *A61F 2250/0039* (2013.01)

(56) References Cited

U.S. PATENT DOCUMENTS

| | | | |
|---|---|---|---|
| 6,723,116 | B2 | 4/2004 | Taheri |
| 6,814,752 | B1 | 11/2004 | Chuter |
| 7,537,606 | B2 | 5/2009 | Hartley et al. |
| 7,645,298 | B2 | 1/2010 | Hartley et al. |
| 9,101,456 | B2 | 8/2015 | Hartley |
| 10,485,651 | B2 * | 11/2019 | Hartley .............. A61F 2/07 |
| 2003/0088305 | A1 | 5/2003 | Van Schie et al. |
| 2003/0199967 | A1 | 10/2003 | Hartley et al. |
| 2005/0102021 | A1 | 5/2005 | Osborne |
| 2005/0131517 | A1 | 6/2005 | Hartley et al. |
| 2006/0184228 | A1 | 8/2006 | Khoury |
| 2008/0109066 | A1 | 5/2008 | Quinn |
| 2008/0281399 | A1 | 11/2008 | Hartley et al. |
| 2009/0048663 | A1 | 2/2009 | Greenberg |
| 2009/0125095 | A1 | 5/2009 | Bui et al. |
| 2009/0248135 | A1 | 10/2009 | Bruszewski et al. |
| 2009/0254170 | A1 | 10/2009 | Hartley |
| 2009/0306763 | A1 | 12/2009 | Roeder et al. |
| 2009/0319022 | A1 | 12/2009 | Hartley |
| 2010/0063576 | A1 | 3/2010 | Schaeffer et al. |
| 2010/0069853 | A1 | 3/2010 | Zukowski |
| 2010/0268327 | A1 | 10/2010 | Bruszewski et al. |
| 2010/0312326 | A1 | 12/2010 | Chuter et al. |
| 2011/0054594 | A1 | 3/2011 | Mayberry et al. |
| 2011/0087319 | A1 | 4/2011 | Hagaman et al. |

FOREIGN PATENT DOCUMENTS

| | | |
|---|---|---|
| JP | 04231954 | 8/1992 |
| JP | 2004298548 | 10/2004 |
| JP | 2005-521471 | 7/2005 |
| JP | 2012-501208 A | 1/2012 |
| WO | WO 2003/082153 A2 | 10/2003 |
| WO | WO2005/032340 | 4/2005 |
| WO | WO 2008/021557 A1 | 2/2008 |
| WO | WO2009/020653 | 2/2009 |
| WO | WO 2010/024879 A1 | 3/2010 |
| WO | WO 2011/159324 A1 | 12/2011 |

OTHER PUBLICATIONS

First Examination Report for Australian Patent Application No. 2011215968 dated Jan. 24, 2013, 2 pgs.
Japanese Office Action/Notification for Reason for Rejection for corresponding JP 2012-552939, dated Dec. 2, 2014, 4 pgs.
Japanese Office Action and English translation for JP Patent Application No. 2012-552939, dated Sep. 8, 2015, 4 pgs.
Notification of Transmittal of the International Search Report and the Written Opinion of the International Searching Authority, International Application No. PCT/US2011/024148, dated Apr. 12, 2011, p. 1-13.
International Preliminary Report on Patentability for PCT/US2011/024148, dated Aug. 14, 2012, 8 pgs.
Canadian Office Action for CA Application No. 2,788,838, dated Jun. 29, 2016, 2 pgs.
Patent Examination Report No. 1 for Australian Patent Application No. 2009286062 dated Feb. 25, 2013, 3 pgs.
Response to Patent Examination Report No. 1 for Australian Patent Application No. 2009286062 filed May 21, 2013, 8 pgs.
Notice of Acceptance for Australian Patent Application No. 2009286062 dated Jul. 8, 2013, 5 pgs.
Patent Examination Report for European Patent Application No. 09789202.0 dated Dec. 14, 2012, 5 pgs.
Patent Examination Report for European Patent Application No. 09789202.0 dated Aug. 5, 2014, 4 pgs.
Reply to Examination Report for European Patent Application No. 09789202.0 filed Jan. 14, 2015, 13 pgs.
Patent Examination Report for European Patent Application No. 09 789 202.0 dated May 28, 2015, 4 pgs.
Reply to Examination Report for European Patent Application No. 09789202.0 filed Aug. 11, 2015, 3 pgs.
Office Action for Japanese Patent Application No. 2011-524987 dated Aug. 14, 2013, 5 pgs. including English translation, 5 pgs.
International Preliminary Reporton Patentability for PCT/US2009/004827 dated Mar. 10, 2011, 8 pgs.
International search report and written opinion for PCT/US2009/004827 dated Nov. 9, 2009, 12 pgs.

\* cited by examiner

THORACIC AORTA STENT GRAFT

RELATED APPLICATIONS

This application is a continuation of U.S. Ser. No. 16/511,516, filed Jul. 15, 2019, which is a continuation of U.S. Ser. No. 16/287,239, filed Feb. 27, 2019, now, U.S. Pat. No. 10,485,651, which is a continuation of U.S. Ser. No. 15/593,715, filed May 12, 2017, now U.S. Pat. No. 10,231,822, which is a continuation of U.S. Ser. No. 13/576,348, filed Jul. 31, 2012, now U.S. Pat. No. 9,649,188, which is a National Stage of International Application No. PCT/US2011/024148, filed Feb. 9, 2011, which claims the benefit of the filing date under 35 U.S.C. § 119(e) of Provisional U.S. Patent Application Ser. No. 61/302,586, filed Feb. 9, 2010. All of the foregoing applications are hereby incorporated by reference in their entirety.

BACKGROUND

1. Technical Field

This invention relates to a medical device for treatment of aortic arch disease and more particularly to a stent graft for deployment into the thoracic aorta of a patient for that purpose.

2. Background Information

In recent years endovascular implantable devices have been developed for treatment of aortic aneurysms. These devices are delivered to the treatment site through the vascular system of the patient rather than by open surgery. The devices include a tubular or cylindrical framework or scaffolding of one or more stents to which is secured a tubular shape of graft material such as woven Dacron, polyester polytetrafluoroethylene or the like. The devices are initially reduced to a small diameter, placed into the leading or proximal end of a catheter delivery system whereafter the delivery system is inserted into the vascular system of the patient such as through a femoral incision. The leading end of the delivery system is manoeuvred to the treatment site over a previously positioned guide wire. Through manipulation of a control system that extends to the proximal end of the catheter from the distal end of the system outside the patient the implantable device is then deployed by holding the device at its location and withdrawing a surrounding sheath. The stent graft or implantable device can then self expand or is expanded through the use of a balloon which is introduced with the stent graft introduction device. The stent graft becomes anchored into position to healthy wall tissue in the aorta such as by barbs whereafter the delivery system is then removed leaving the device in position to reverse an aneurysm in the aorta in a manner that channels all blood flow through the stent graft so that no blood flow enters the aneurysm thereafter, such that not only does the aneurysm no longer continue to grow and possibly rupture but the aneurysm actually begins to shrink and commonly disappears entirely.

For treatment of thoracic aortic aneurysms in particular it is necessary to introduce the implantable device high up in the aorta and in a region of the aorta which is curved and where there can be strong blood flow.

In the thoracic aorta there are major branch vessels, the brachiocephalic, the left carotid and the left subclavian and for treatment of an aneurysm in the region of the thoracic arch provision must be made for blood supply to continue to these arteries. For this purpose fenestrations are provided into the wall of a stent graft in that region. Access is generally obtained to these fenestrations, to deploy side arms into the stent graft, via the left or right brachial arteries or less commonly via the left or right carotid arteries. Once into the thoracic arch via such an artery the fenestration in the stent graft must be catheterised.

If a stent graft has been deployed into the thoracic aorta around the arch such that its fenestrations are not aligned precisely with their corresponding great vessels of the arch, then it can be difficult to access the fenestrations through corresponding vessels (such as the brachiocephalic and the left brachial arteries).

It is the object of this invention to provide an arrangement of stent graft to overcome the above problem or to at least provide the practitioner with a useful alternative.

Throughout this specification the term distal with respect to a portion of the aorta, a deployment device or a prosthesis such as a stent graft is intended to mean the end of the aorta, deployment device or prosthesis such as a stent graft further away in the direction of blood flow from the heart and the term proximal is intended to mean the portion of the aorta, deployment device or end of the prosthesis nearer to the heart. For other lumens within the human or animal body the terms caudal and cranial respectively should be understood.

Throughout this discussion the term "stent graft" is intended to mean a device which has a tubular body of biocompatible graft material and at least one stent fastened to the tubular body to define a lumen through the stent graft. The stent graft may be bifurcated and have fenestrations, side arms or the like. Other arrangements of stent grafts are also within the scope of the invention.

BRIEF SUMMARY

In one form therefore the invention is said to reside in a stent graft for placement in the thoracic arch of a patient, the stent graft comprising:

a tubular body defining a main lumen therethrough, a plurality of zig zag stents along the tubular body, each of the stents comprising a plurality of struts and bends, the bends being between adjacent struts;

at least a first stent and an adjacent second stent, the first and second stents having at least a pair of adjacent bends on the first stent aligned with an adjacent pair of bends on the second stent, whereby a first pair of adjacent struts of the first stent and a second pair of adjacent struts of the second adjacent stent together define a diamond shaped region;

a recess in the diamond shaped region, the recess being defined by a concave portion of graft material and the recess extending into the lumen of the tubular body, the recess having a proximal end;

a fenestration in the concave portion of graft material, the fenestration opening into the tubular body within the recess in the diamond shaped region; and a graft tube leading from the fenestration into the main lumen.

Preferably the fenestration and graft tube extend from the proximal end of the recess.

In one form the stent graft further comprises:

a third adjacent stent, the third adjacent stent having at least a pair of bends adjacent to the second stent whereby a third pair of adjacent stents of the third strut defines a second diamond shaped region, wherein the second diamond shaped region shares a strut with the first diamond shaped region.

Preferably the stent graft comprises one, two or three diamond shaped regions, each diamond shaped region comprising a respective recess, fenestration and graft tube.

Preferably the stent graft comprises a proximal end and a distal end and the, or each, graft tube extends within the main lumen towards the proximal end of the stent graft.

Preferably the bends and adjacent struts define an included angle in the range of from 40 to 80 degrees.

Preferably proximally of the diamond shaped region the tubular body has a first diameter, distally of the diamond shaped region the tubular body has a second diameter and in a region of the tubular body around the diamond shaped region the tubular body has a third diameter, the first diameter being greater than the second diameter and both the first and second diameter being greater than the third diameter whereby a central region is defined which will allow at least part circumferential blood flow during an operation out of the graft tube into the recess and then into the central region.

It will be seen that by this invention there is provided a stent graft for placement in the thoracic arch of a patient. The stent graft can be placed such that the intermediate portion is just proximal of the brachiocephalic artery and on the outside of the curve of the thoracic arch. By this placement there is defined, by the difference in diameter of the first and second portions, an open region outside the stent graft distal of the aperture in the step portion, so that blood flow can occur through the aperture to the open region enabling circulation to be preserved to the major vessels through the internal branches during the progress of an operation. As the intermediate portion is of stent graft is of a lesser diameter there is provided a working space in the recess in which a guide wire from the branch arteries can be directed to enter the internal tube to enable catheterisation. Subsequently a side branch stent graft can be deployed from the respective branch artery into the tube to provide blood flow into that branch artery.

In a preferred embodiment the first diameter can be from 35 to 50 mm, the second diameter can be from 40 to 30 mm, the third diameter can be from 20 to 40 mm. For instance in one embodiment the first diameter is 46 mm and the second and third diameters are 38 mm. In another embodiment the first and third diameters are 36 mm and the third diameter is 24 mm.

In one form the stents are formed from nitinol.

In one form the or each graft tube comprises a reinforcement in the form of a space frame.

In one form the space frame comprises a cylindrical portion the cylindrical portion comprising first and second circular ring portions spaced apart axially and at least two struts extending between the first and second circular ring portions and the graft tube being around the space frame.

In one form the cylindrical portion comprises an assembly of two individual ring and strut components, each ring and strut component comprising a circular ring portion defining a plane of the circular ring portion and a strut extending at right angles to the plane of the circular ring portion from a periphery of the circular ring portion.

In an alternative form the invention is said to reside in a stent graft for placement in the thoracic arch of a patient, the stent graft comprising:

a tubular body defining a main lumen therethrough, a plurality of zig zag stents along the tubular body, each of the stents comprising a plurality of struts and points or bends, the points or bends being between adjacent struts;

a shaped recess in the tubular body having a perimeter, the perimeter being formed at least in part at two adjacent struts of a first stent and two adjacent struts of a second adjacent stent;

the shaped recess being defined by a concave portion of graft material and the shaped recess extending into the lumen of the tubular body, the shaped recess having a proximal end;

a fenestration in the concave portion of graft material, the fenestration opening into the tubular body within the shaped recess; and a graft tube leading from the fenestration into the main lumen.

Preferably the fenestration and graft tube extend from the proximal end of the shaped recess.

In one form the stent graft further comprises:

a second shaped recess in the tubular body defined by a second perimeter, the second perimeter being formed at least in part at two adjacent struts of the second stent and two adjacent struts of a third adjacent stent.

In one form the stent graft further comprises: a proximal end and a distal end and the or each graft tube extends within the main lumen towards the proximal end of the stent graft.

Preferably the bends and adjacent struts define an included angle in the range of from 40 to 80 degrees.

In one form the stents are formed from nitinol.

In one form the or each graft tube comprises a reinforcement in the form of a space frame.

In one form the space frame comprises a cylindrical portion the cylindrical portion comprising first and second circular ring portions spaced apart axially and at least two struts extending between the first and second circular ring portions and the graft tube being around the space frame.

In one form the cylindrical portion comprises an assembly of two individual ring and strut components, each ring and strut component comprising a circular ring portion defining a plane of the circular ring portion and a strut extending at right angles to the plane of the circular ring portion from a periphery of the circular ring portion.

In a further alternative form the invention is said to reside in a stent graft for placement in the thoracic arch of a patient, the stent graft comprising:

a tubular body defining a main lumen therethrough, a plurality of zig zag stents along the tubular body, each of the stents comprising a plurality of struts and bends, the bends being between adjacent struts;

at least a first stent and an adjacent second stent, the first and second stents having at least a pair of adjacent bends on the first stent aligned with an adjacent pair of bends on the second stent, whereby a first pair of adjacent struts of the first stent and a second pair of adjacent struts of the second adjacent stent together define a diamond shaped region;

a recess in the diamond shaped region, the recess being defined by a concave portion of graft material and the recess extending into the lumen of the tubular body, the recess having a proximal end;

a fenestration in the concave portion of graft material, the fenestration opening into the tubular body within the recess in the diamond shaped region; and a graft tube leading from the fenestration into the main lumen, the fenestration and graft tube extending from the proximal end of the recess towards the proximal end of the stent graft.

BRIEF DESCRIPTION OF THE DRAWINGS

This then generally describes the invention but to assist with understanding reference will now be made to the accompanying drawings which show preferred embodiments of the invention.

In the drawings.

DETAILED DESCRIPTION OF THE DRAWINGS AND THE PRESENTLY PREFERRED EMBODIMENTS

Figure 5:
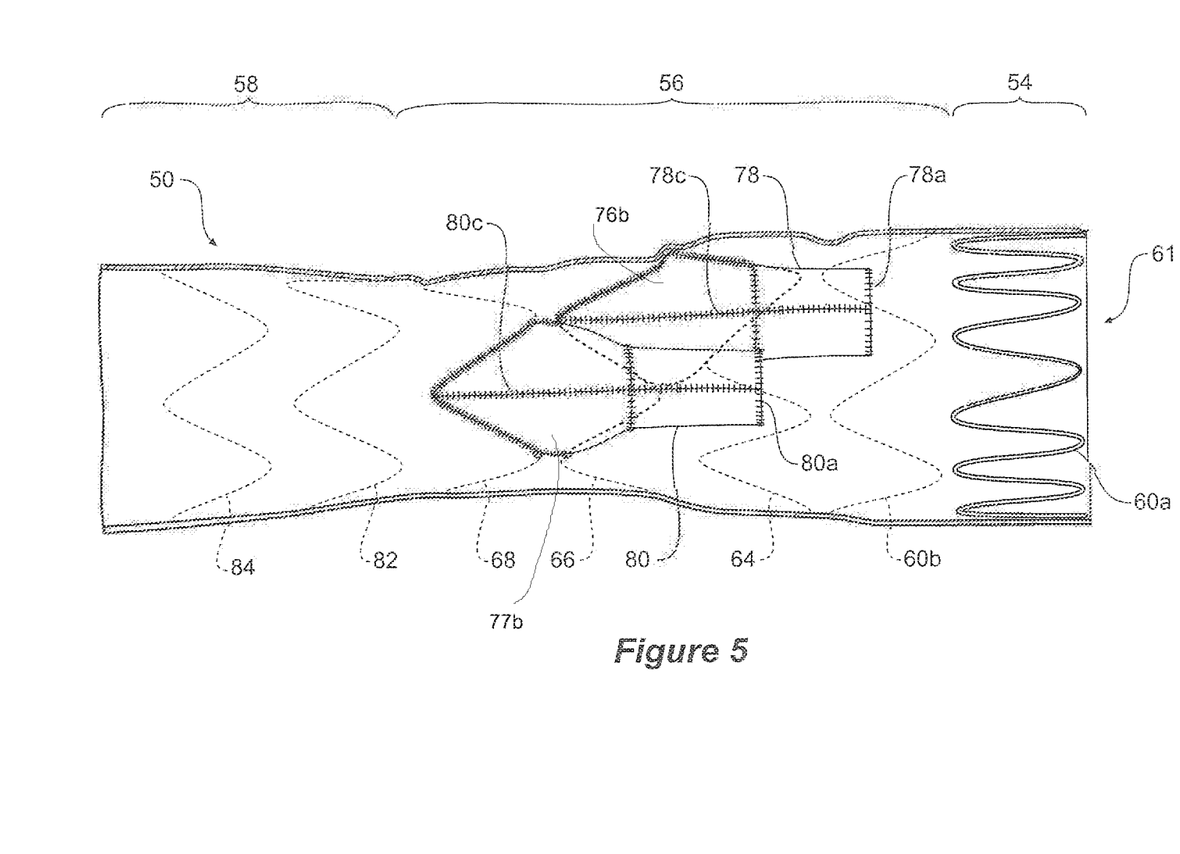
FIG. 5 shows a longitudinal cross-sectional view of the stent graft shown in FIG. 1.

FIGS. 1 to 6 show an embodiment of stent graft according to the present invention. In this embodiment the tubular body 52 of this embodiment of stent graft 50 comprises a proximal portion 54, an intermediate portion 56 and a distal portion 58 as shown in FIG. 5.

Figure 1:
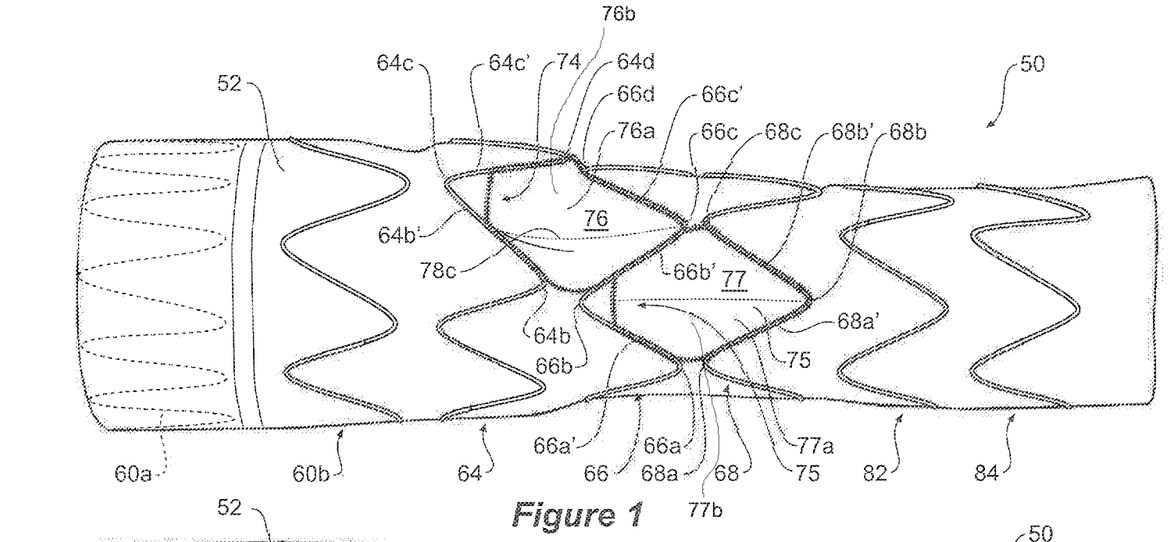
FIG. 1 shows a plain view of a first embodiment of a stent graft according to the present invention.

Referring to FIG. 1 it can be seen that the proximal portion 54 comprises a tubular body of a biocompatible graft material and is supported by self expanding zig zag stents 60a and 60b. The stent 60a is internal to provide a smooth sealing surface to engage against the wall of the ascending aorta, and the stent 60b is external. The proximal portion may have a diameter from 35 to 50 mm.

The distal portion 58 is again formed from a tubular body of a biocompatible graft material and is supported by self expanding zig zag stents 82 and 84. The distal portion 58 can have a diameter in the range of from 30 to 40 mm.

The intermediate portion 56 is supported by self expanding zig zag stents 64 and 66 and is the region into which are placed the diamond shaped regions and the recess according to the present invention. The intermediate portion has a diameter in the range from 20 to 30 mm and had tapered portions at each end to connect with the proximal and distal portions respectively.

The stents 64, 66 and 68 comprise a plurality of struts and bends, the bends between the adjacent struts. In the embodiment shown, the struts are substantially longer than the bends, the bends having a relatively small radius. The stents are made from shape memory wire in the form of nitinol (metal alloy of nickel and titanium).

The intermediate portion 56 has a diameter at its proximal end 61 which is substantially the same as the diameter of the proximal portion 54 and a diameter at its distal end which is substantially the same as the diameter of the distal portion 58. The intermediate portion 56 has most, if not all of its taper between the diameter of the proximal portion and the diameter of the distal portion on the outside 72 of the curve of the stent graft.

Figure 2:
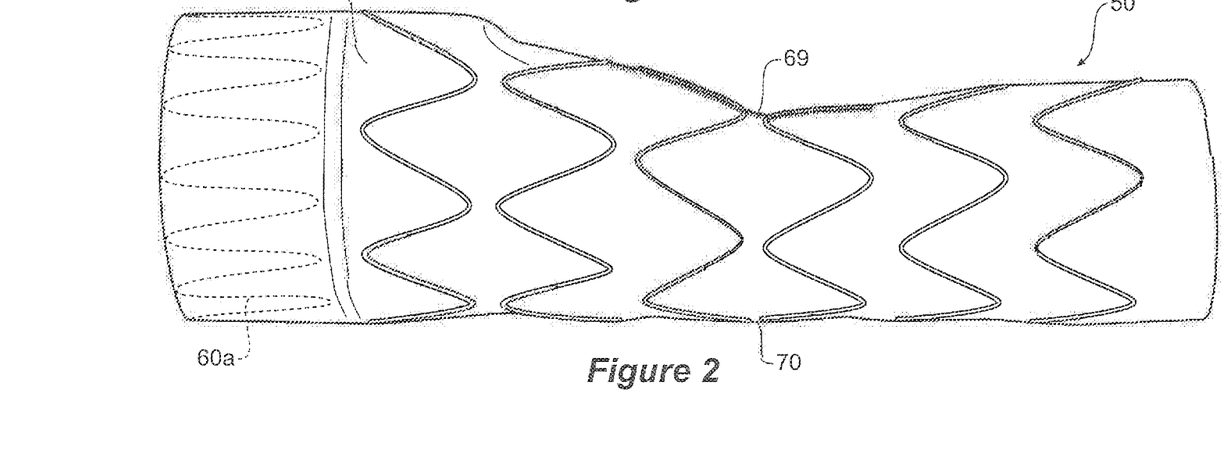
FIG. 2 shows a side view of the stent graft of FIG. 1.

As can be seen in FIG. 1 the intermediate portion 56 has two apertures or fenestrations 74 and 75 which open into respective recesses 76 and 77 within the step portion and graft tubes from the recesses extends proximally towards the proximal portion 54. As shown in FIGS. 1 and 2, the recesses 76 and 77 are inclined relative to the longitudinal axis of the stent graft.

Adjacent stents 64 and 66 are positioned such that they define a diamond shape region 76a. The diamond shape arises from having a pair of distal bends 64b and 64d of stent 64 aligned with a pair of proximal bends 66b and 66d of stent 66 as is clearly shown in FIG. 1. A first pair of adjacent struts 64b' and 64c' of stent 64 and a second pair of adjacent struts 66b' and 66c' of the adjacent stent 66 together define a diamond shaped region 76a.

A recess 76 lies within the diamond shape region 76a. A fenestration 74 into the tubular body leads from recess 76 into a graft tube 78. The graft tube 78 extends within the tubular body towards a proximal end of the stent graft as is most clearly shown in the cross-sectional view of FIG. 5.

A third adjacent stent 68 has a pair of bends 68a and 68c adjacent to the second stent 66 such that a third pair of adjacent stents 68a' and 68b' define a second diamond shape region 77a. The second diamond shape region 77a shares a strut 66b' with the first diamond shape region 76a.

Figure 6:
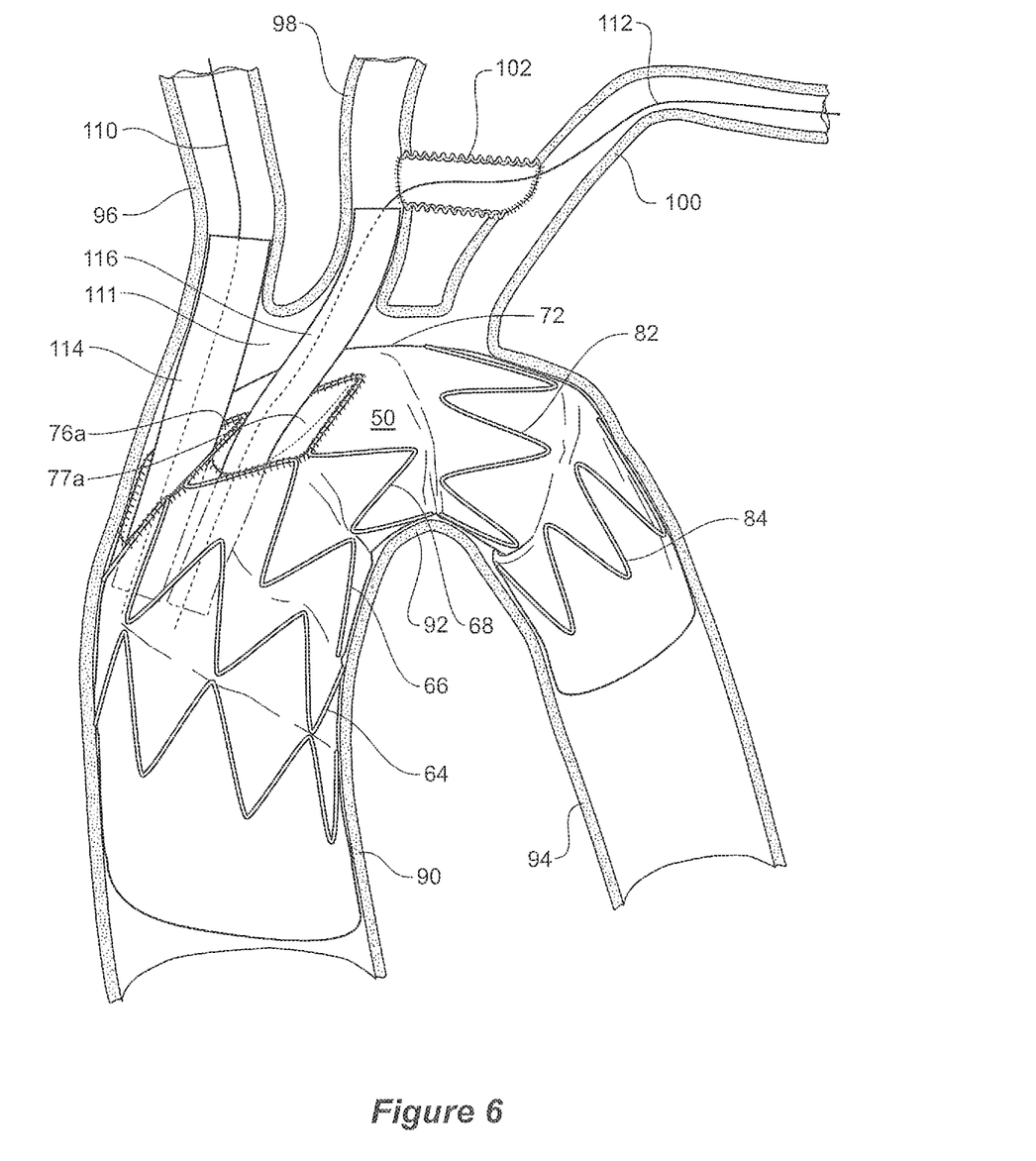
FIG. 6 shows a schematic view of the placement of a stent graft according to the present invention into the thoracic arch of a patient.

In this particular embodiment stent 64 has fourteen bends (seven distal bends and seven proximal bends) and stent 66 has twelve bends (six distal bends and six proximal bends). As a result of the differing number of bends and the alignment described above, distal bends of stent 64 are not aligned with proximal bends of stent 66 at the inside radius of the stent graft, the side of the stent graft without the diamond shaped regions, when it is placed in the arch as illustrated in FIG. 6. This assists in providing flexibility so as to facilitate the stent graft conforming to the anatomy of the thoracic arch as is shown in FIG. 6. In other embodiments different numbers of struts and bends may be used. In general, however, it is preferable for adjacent stents to have different numbers of struts and bends so that on the side of the stent graft without the fenestrations and recesses the bends do not coincide thereby allowing better flexibility.

The diamond shape regions and recesses 76a and 77a facilitate insertion of guide wires from the major branch arteries (such as the brachiocephalic and the left carotid artery) into the internal tubes 78 and 80 of the stent graft 50.

With the embodiment shown in FIGS. 1 to 6, the diamond shape regions 76a and 77a are adjacent each other and are separated by a strut 66b' of stent 66. With this arrangement, the corresponding fenestrations 74 and 75 are offset from each other so that one is slightly more ventral than the other with respect to the thoracic arch.

The recess 76 within the intermediate portion 56 opens at its proximal end into a tube 78 and the recess 77 opens at its proximal end into a tube 80. Each of the tubes may be of the same diameter or the uppermost of the tubes 78 may have a diameter which is greater than the diameter of the lower tube 80. The tubes 78 and 80 extend towards the proximal end 61 of the stent graft 50.

The proximal end of the tubes 78 and 80 are held open by reinforcing wires, or wire portions, 78a and 80a respectively, these wires arranged to form circles as is shown in the cross-sectional view of FIG. 5.

Figure 3:
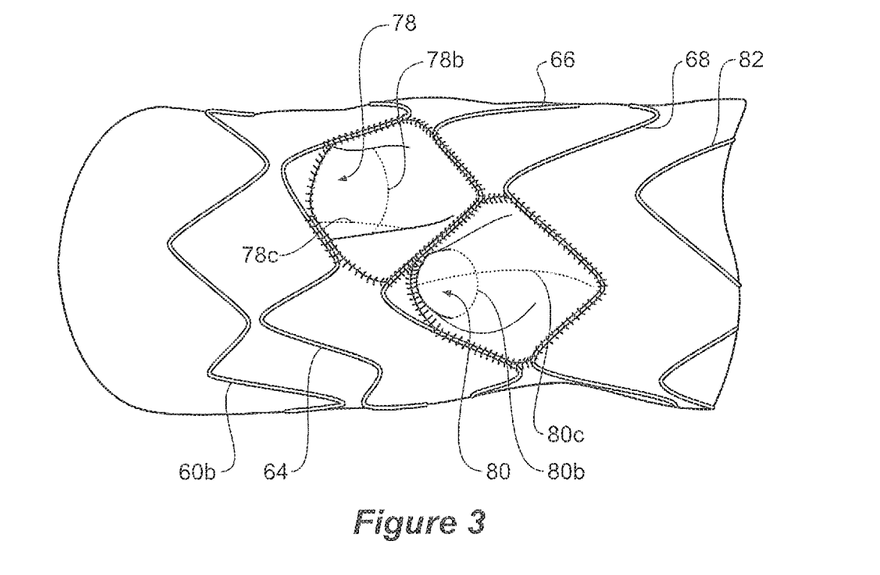
FIG. 3 is an isometric view looking in a slightly distal direction along the stent graft of FIG. 2.
Figure 4:
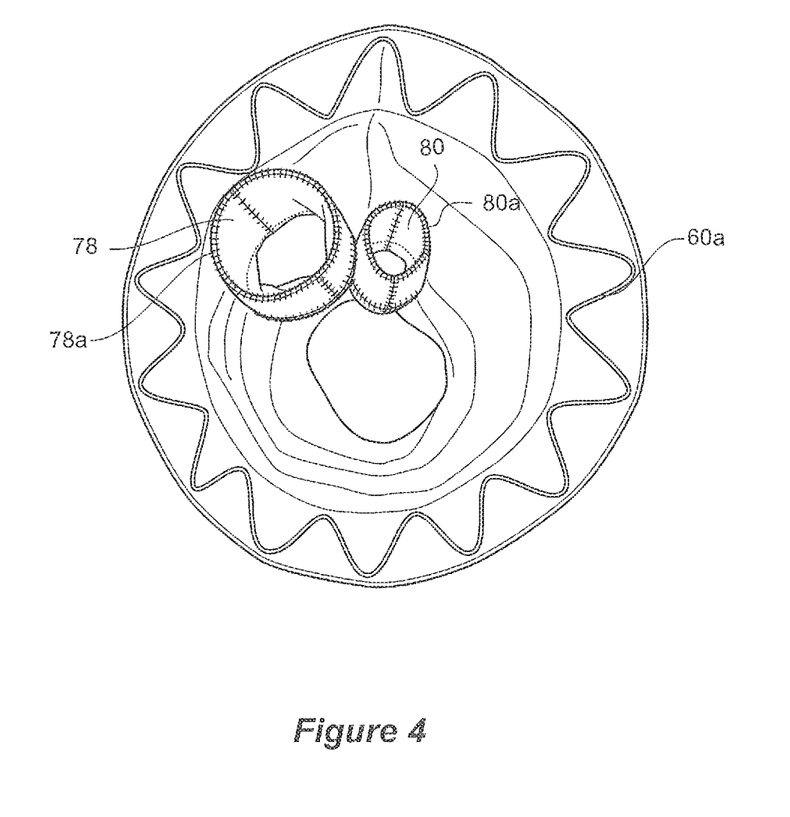
FIG. 4 shows a view from the proximal end of the stent graft shown in FIG. 1.

The tubes 78 and 80 also have reinforcing wires, or wire portions, 78b and 80b arranged to hold the respective distal ends of the tubes open as is more clearly shown in FIG. 3.

Extending from reinforcing wire 78a, past reinforcing wire 78b and to bend 66c is a longitudinal reinforcing wire, or wire portion 78c as is most clearly shown in FIG. 1. Similarly, extending from reinforcing wire 78a, past reinforcing wire 80a and to bend 68b is a longitudinal reinforcing wire, or wire portion 80c.

Each of the smaller internal tubes 78 and 80 can be reinforced with a helical shape memory wire reinforcement. Helical reinforcement for graft material is shown in U.S. patent application Ser. No. 12/261,860 entitled "Flexible Stent Graft" and the teachings therein are incorporated herein in their entirety.

FIG. 6 shows a schematic view of the placement of a stent graft according to one embodiment of the present invention into the thoracic arch of a patient.

The thoracic arch shown schematically comprises an ascending aorta 90 extending to the thoracic arch 92 and a descending aorta 94 from the thoracic arch. Substantially at the top of the thoracic arch but slightly to the ventral side of the arch the major vessels branch off the arch. The major vessels are the brachiocephalic artery 96, the left common carotid artery 98 and the left subclavian 100. In a preparatory operation an anastomosis 102 is provided between the common carotid artery 98 and the left subclavian 100. The anastomosis provides access between the common carotid artery 98 and the left subclavian artery 100 which enables endovascular access to the stent graft via brachial arteries in the left arm rather than endovascular access via the left carotid artery which may be more complex.

The stent graft 50 is deployed into the thoracic arch such that the intermediate portion 56 is just proximal of the junction of the aorta with the brachiocephalic artery 96. This means that there is defined between the intermediate portion 56, the upper wall of the thoracic arch and the distal portion 58 of the stent graft 50, an open region 111 so that circulation can be preserved to the major vessels through the internal tubes 78 and 80 and the recess 76 (see FIGS. 3 and 4) during the operation of deployment of the stent graft and subsequent placement of side branch grafts. The space also assists in enabling catheterisation of the internal tubes. A catheter 110 can be inserted to enter the larger of the tubes 78 to enable placement of a side branch stent graft 114 for the brachiocephalic artery 96 and a catheter 112 can be inserted to enter the smaller of the tubes 80 to enable placement of a side branch stent graft 116 for the common carotid artery 98 and the left subclavian artery 100. Subsequently a side branch stent graft can be deployed from the respective branch artery into one of the smaller tubes to provide blood flow into that branch artery.

Because the space 111 provides maintenance of circulation to the major vessels there may be circumstances where an operation can be carried out in stages.

In a preferred embodiment the larger of the internal tubes 78 has a diameter of from 8 to 12 mm and the smaller of the tubes has a diameter of from 8 to 10 mm.

The graft tubes extending into the main lumen can have a reinforcement in the form of a space frame. The components of the space frame can be an assembly of two ring and strut components. Each ring and strut component comprises a circular ring portion defining a plane of the circular ring portion and a strut extending at right angles to the plane of the circular ring portion from a periphery of the circular ring portion. Each of the two ring and strut components are formed from a single length of a rigid but resilient wire such as a nickel titanium alloy wire. At each end of each piece of wire a loop is formed to ensure that a sharp end which could puncture a vessel wall is not present. Once the components of the lightweight space frame are formed they have stitched to them portions of biocompatible graft material to form separately the tubular portion 78, 80 and the enlarged funnel portion 76b, 77b and then these are joined together by stitching or the like to form the internal tubes or branches 78, 80 and the recesses 76, 77. FIGS. 5 and 6 show the tubular portions 78, 80 and enlarged funnel portions 76b, 77b as they are attached to the graft to form the recesses and internal branches.

Figure 7:
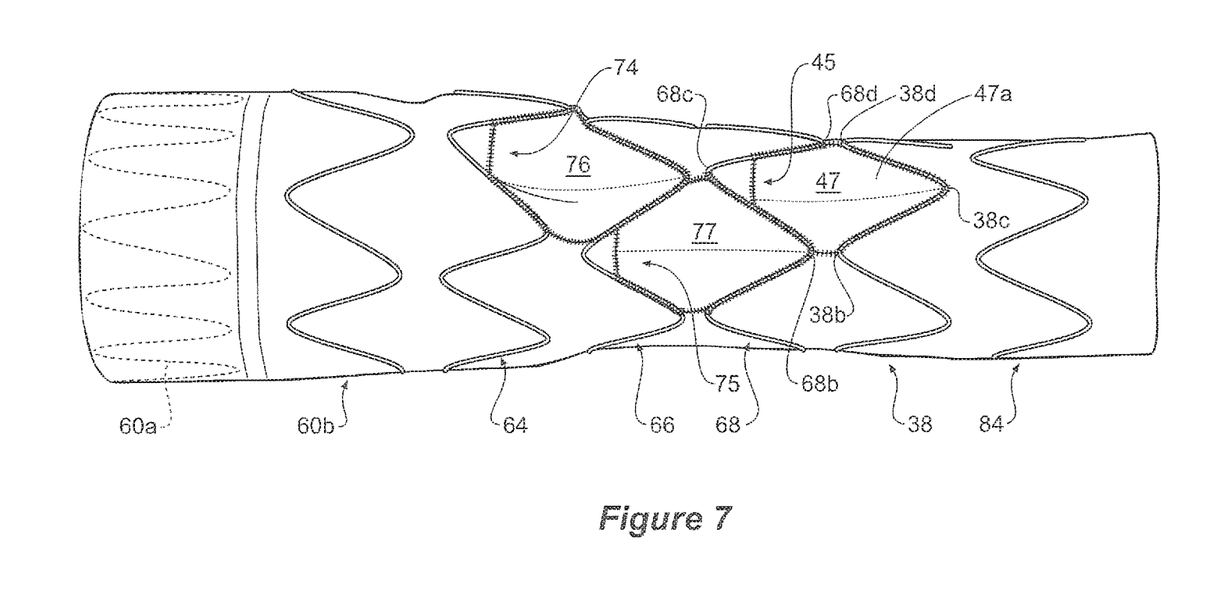
FIG. 7 shows a plan view of a second embodiment of a stent graft according to the present invention.

FIG. 7 shows an alternative embodiment. This embodiment is similar to that shown in FIGS. 1 to 6 but it includes a third diamond shaped region 47a with its corresponding recess 47 and fenestration 45. In other embodiments, not shown, there can be a single diamond shaped region, multiple diamond shaped regions aligned longitudinally or other layouts of the regions. As further shown in FIGS. 1, 5, 6 and 7, the recesses 47, 76 and 77 are oblong and have two sides tapering or converging toward the fenestrations of the internal branches and two sides tapering or converging toward the distal end of the recess. As shown, the first two sides tapering or converging toward the fenestration are shorter than the sides tapering or converging toward the distal ends of the recesses.

Many modifications and other embodiments of the invention will come to the mind of one skilled in the art having the benefit of the teachings presented in the foregoing descriptions and associated drawings. Therefore, it is understood that the invention is not to be limited to the specific embodiments disclosed, and that modifications and embodiments are intended to be included within the scope of the appended claims.

The invention claimed is:

1. A stent graft for placement in a vessel of a patient, the stent graft comprising:
   a tubular body, the tubular body having a first end, a second end, a main lumen therethrough, and a sidewall from the first end to the second end;
   a plurality of stents along the tubular body, including a first stent and a second stent adjacent the first stent;
   a first recessed region in the tubular body, the first recessed region defined by a first portion of graft material that extends into the main lumen of the tubular body;
   a second recessed region in the tubular body, the second recessed region defined by a second portion of graft material that extends into the main lumen of the tubular body, wherein the first recessed region and the second recessed region share a common border;
   a third recessed region in the tubular body, the third recessed region defined by a third portion of graft material that extends into the main lumen of the tubular body, wherein the second recessed region and the third recessed region share a common border;
   a first fenestration in the first recessed region, a second fenestration in the second recessed region, a third fenestration in the third recessed region, each of the first, second, and third fenestrations opening into the main lumen of the tubular body;
   a first graft tube leading from the first fenestration into the main lumen toward the second end, a second graft tube leading from the second fenestration into the main lumen toward the second end, and a third graft tube leading from the third fenestration into the main lumen toward the second end.

2. The stent graft of claim 1, wherein each of the first, second, and third recessed regions have a first end and a second end and each of the first, second, and third fenestrations are disposed in the second end of its respective recessed region.

3. The stent graft of claim 2, wherein the second and third recessed regions are at least partially longitudinally and circumferentially offset from each other, and the first and third recessed regions are at least partially longitudinally offset from each other.

4. The stent graft of claim 1, wherein the first and second fenestrations are at least partially circumferentially and longitudinally offset from each other.

5. The stent graft of claim 4, wherein the second and third fenestrations are at least partially circumferentially and longitudinally offset from each other and the first and third fenestrations are at least partially longitudinally offset from each other.

6. The stent graft of claim 1, wherein the first recessed region is configured to be aligned with a left subclavian artery, the second recessed region is configured to be aligned with a left common carotid artery, and the third recessed region is configured to be aligned with a brachiocephalic artery.

7. The stent graft of claim 1, wherein each of the first, second, and third recessed regions have a polygonal shape.

8. A stent graft for placement in a vessel of a patient, the stent graft comprising:
   a tubular body, the tubular body having a first end, a second end, a main lumen therethrough, and a sidewall;
   a plurality of stents along the tubular body, including a first stent and a second stent adjacent the first stent;
   a first recessed region in the tubular body, the first recessed region defined by a first recessed portion of graft material that extends into the main lumen of the tubular body;
   a second recessed region defined by a second recessed portion of graft material that extends into the main lumen of the tubular body, wherein the first recessed region abuts the second recessed region;
   a third recessed region defined by a third recessed portion of graft material that extends into the main lumen of the tubular body, wherein the second recessed region abuts the third recessed region;
   a first fenestration in the first recessed region, a second fenestration in the second recessed region, a third fenestration in the third recessed region, each of the first, second, and third fenestrations opening into the tubular body;
   a first graft tube leading from the first fenestration into the main lumen towards an end of the stent graft, a second graft tube leading from the second fenestration into the main lumen towards the end of the stent graft, and a third graft tube leading from the third fenestration into the main lumen towards the end of the stent graft, wherein the end of the stent graft is the same end.

9. The stent graft of claim 8, where the end of the stent graft is the second end.

10. The stent graft of claim 8, wherein the second and third fenestrations are at least partially circumferentially and longitudinally offset from each other.

11. The stent graft of claim 8, wherein the first recessed region is configured to be aligned with a left subclavian artery, the second recessed region is configured to be aligned with a left common carotid artery, and the third recessed region is configured to be aligned with a brachiocephalic artery.

12. The stent graft of claim 8, wherein the first recessed region and the second recessed region share a common border.

13. The stent graft of claim 8, wherein the second recessed region and the third recessed region share a common border.

14. The stent graft of claim 8, wherein each of the first, second, and third recessed regions have a polygonal shape.

15. A stent graft for placement in a vessel of a patient, the stent graft comprising:
   a tubular body of graft material, the tubular body having a main lumen therethrough, the graft material defining a side wall, and a plurality of discrete stents along the tubular body, the stents comprising:
   a first stent of the plurality of stents, a second stent of the plurality of stents adjacent to the first stent, a third stent of the plurality of stents adjacent to the second stent, and a fourth stent, wherein the first and second stents are aligned to define a first shaped region, the second and third stents are aligned to form a second shaped region, and the third and fourth stents are aligned to define a third shaped region;
   a first recess in the first shaped region, the first recess being defined by a first recessed portion of graft material that extends into the main lumen of the tubular body, the first recess having a first end;
   a second recess in the second shaped region at least partially longitudinally and circumferentially offset from the first recess, the second recess being defined by a second recessed portion of graft material that extends into the main lumen of the tubular body, the second recess having a first end;
   a third recess in the third shaped region at least partially longitudinally and circumferentially offset from the second recess and longitudinally offset from the first recess, the third recess being defined by a third recessed portion of graft material that extends into the main lumen of the tubular body, the third recess having a first end;
   a first fenestration disposed at the first end of the first recess, the first fenestration opening into the lumen of the tubular body from the first recessed portion;
   a second fenestration disposed at the first end of the second recess, the second fenestration opening into the lumen of the tubular body from the second recessed portion;
   a third fenestration at the first end of the third recess, the third fenestration opening into the lumen of the tubular body from the third recessed portion;
   a first graft tube leading from the first fenestration into the main lumen and towards an end of the stent graft;
   a second graft tube leading from the second fenestration into the main lumen towards the end of the stent graft;
   a third graft tube leading from the second fenestration into the main lumen towards the end of the stent graft.

16. The stent graft of claim 15, wherein each of the first, second, and third shaped regions has a greater longitudinal dimension than a circumferential dimension.

17. The stent graft of claim 15, wherein each of the first, second, and third shaped regions has a border, wherein the first and second shaped regions share a common border and the second and third regions share a common border.

18. The stent graft of claim 17, wherein the common border shared by the first and second shaped regions comprises at least one strut of the second stent.

19. The stent graft of claim 18, wherein the common border shared by the second and third shaped regions comprises at least one strut of the third stent.

20. The stent graft of claim 15, wherein the first, second, and third shaped regions are polygonal.

21. The stent graft of claim 15, wherein the first and second shaped regions are at least partially offset from each other both longitudinally and circumferentially, and the second and third shaped regions are at least partially offset from each other both longitudinally and circumferentially.

* * * * *